United States Patent [19]

Waali

[11] Patent Number: 4,663,151

[45] Date of Patent: May 5, 1987

[54] ALUMINUM CHLORHYDRATE AS A PROPHYLATIC TREATMENT FOR POISON OAK, POISON IVY AND POISON SUMAC DERMATITIS

[75] Inventor: Edward E. Waali, Missoula, Mont.

[73] Assignee: Research Corporation, N.Y.

[21] Appl. No.: 776,332

[22] Filed: Sep. 16, 1985

[51] Int. Cl.$^4$ .............................................. A61K 33/06
[52] U.S. Cl. ..................... 424/45; 424/154; 514/862
[58] Field of Search .................. 424/45, 154; 514/862

[56] References Cited

PUBLICATIONS

Handbook of Nonprescription Drugs, 5th ed., 1977, pp. 343–346.

Merck Index, 9th ed., 1976, pp. 47, #342.

*Primary Examiner*—Leonard Schenkman
*Attorney, Agent, or Firm*—Scully, Scott, Murphy & Presser

[57] ABSTRACT

A method for the use of aluminum chlorhydrate to prevent the dermatitis or skin irritation caused by exposure to urushiol oil of a plant of the genera Toxicodendron or Rhus. Various methods of prevention and preventing of spreading of the symptoms of the dermatitis are also disclosed.

16 Claims, No Drawings

ALUMINUM CHLORHYDRATE AS A PROPHYLATIC TREATMENT FOR POISON OAK, POISON IVY AND POISON SUMAC DERMATITIS

GOVERNMENT SUPPORT

The invention described herein was made in the course of work under a grant or award from the U.S. Department of Agriculture, Forest Service, Grant Nos. PO# 43-0343-2-1408 and PO# 40-0343-4-1326.

BACKGROUND OF THE INVENTION

1. Field of the Invention

This invention relates to a method of preventing poison oak, poison ivy and poison sumac dermatitis. More specifically, the invention relates the use of aluminum chlorhydrate as a prophylatic to prevent the diseases described above by application to the skin and fomites.

2. Discussion of the Prior Art

Poison oak, ivy or sumac dermatitis is caused by contact of the skin with the sap of these plants. An oil present in the sap, called urushiol oil, contains the irritating compounds. These chemicals are various 3-alkenylcatechols and 3-alkylcatechols. Their chemical structures have been known for some time and are relatively simple. The catechol and aliphatic portions of the structures are necessary for their activity. The chemicals are generically described by the following formula:

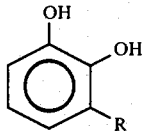

wherein R is an alkyl or alkenyl group of 15 to 17 carbon atoms. The exact composition of the urushiol depends on the plant source and the part of the plant from which the urushiol comes.

Poison oak or poison ivy grows in almost every state, usually at elevations below 4,000 feet. The leaves vary in morphology with urushiol being present in the leaves, stem and roots.

The sap is not normally found on the undamaged leaf; the plant must be damaged for the sap to contact the skin. Uninjured leaves are not harmful. Although this is an academic point under most conditions of exposure, it does emphasize the fact that when the plants are being cut, the most toxic part is the cut end of the stem, and the crushed leaves. Potency of the plant may vary at different times of the year, but it is not enough to make a difference in the reaction of sensitive individuals. The urushiol oil is heavy and is not vaporous or gaseous. However, when the plant is burned, the heavy oil coats the soot, and this airborne material is dangerous to people downwind from the fire. This exposure can often produce severe dermatitis.

A common way of acquiring the dermatitis, apart from contact with the plant, is through fomites, i.e., objects that can carry the oil. Clothes, tools, equipment, animals and the like are fomites. The oil present on the fomites may remain active for months or even years and slowly becomes inactive by oxidation or polymerization.

The oil is not immediately irritating. In sensitive persons, their immune system recognizes the oil as foreign and mounts an inflammatory response. Six to twenty-four hours after contact itching is manifested as the first symptom. This is followed by redness and swelling up to forty eight hours after contact. Eventually, microblisters coalesce forming weepy, itching lesions that can be incapacitating. The intensity of the reaction depends on individual sensitivity and the concentration of the oil at each site on the skin. About fifty percent of the population of the United States is sensitive to urushiol.

U.S. Pat. No. 3,922,342 to Rathbun describes a method for the removal from the skin of the active phenolic compounds of an individual exposed to the oil of poison ivy and oak. The method utilizes hydrophilic anion exchange material applied topically to the affected skin area in a suitable carrier. After a sufficient contact time, the anion exchange material is removed and discarded. The treated area is rinsed with water and dried.

U.S. Pat. No. 3,875,301 to Windheuser describes a process for treating the skin and relieving the symptoms caused by poison oak or ivy by the topical application of certain tetraalkyl diamines.

U.S. Pat. No. 3,862,331 to Crary describes a process for treating the skin and relieving the symptoms caused by poison oak or ivy by the topical application of 2-butanone.

U.S. Pat. No. 3,749,772 to Cardarelli, et al. describes a composition which prevents skin irritation caused by contact with poison ivy or oak. The composition is based upon a film-forming acrylic polymer and includes a linking agent, so that upon application in a solvent carrier to the skin a selective membrane is formed.

While the art has provided various methods and compositions for preventing and relieving the dermatitis caused by exposure to the oil of poison ivy or oak, the need still exists for a method of preventing the skin irritation or dermatitis caused by the oil of a plant of the genera Toxicodendron or Rhus from direct or indirect contact. For example, present methods are generally directed to the relieving symptoms of dermatitis caused by a plant of the genera Toxicodendron or Rhus, rather than preventing the dermatitis or skin irritation caused by a plant of the genera Toxicodendron or Rhus.

Accordingly, it is one object of the present invention to provide a method of preventing the dermatitis or skin irritation caused by the oil of a plant of the genera Toxicodendron or Rhus.

Another object of the present invention herein is to provide a new method of preventing the dermatitis or skin irritation caused by the oil of plant of the genera Toxicodendron or Rhus by the topical application of an efficacious composition to the skin.

A further object of this invention is to provide a new method of preventing the dermatitis or skin irritation caused by the oil of a plant of the genera Toxicodendron or Rhus by the application of an efficacious composition to fomites.

A still further object of this invention is to provide a method of preventing the spread of symptoms of the dermatitis or skin irritation caused by exposure to the oil of a plant of the genera Toxicodendron or Rhus.

The achievement of these and other objects will be apparent from the following description of the subject invention.

SUMMARY OF THE INVENTION

These and other objects are achieved by preventing the dermatitis or skin irritation caused by contact with the oil of a plant of the genera Toxicodendron or Rhus. Briefly, this invention relates to a method of preventing the dermatitis or skin irritation caused by contact with the oil of a plant of the genera Toxicodendron or Rhus by the topical application of an efficacious composition to the skin or application of an efficacious composition to fomites. Specifically, this invention relates to a method of preventing dermatitis or skin irritation in animals caused by the exposure of animal skin or fur to the oil of a plant of the genera Toxicodendron or Rhus which comprises the topical application to exposed skin or fur of an efficacious amount of aluminum chlorhydrate.

In another embodiment, this invention relates to a method of preventing the dermatitis or skin irritation in animals caused by exposure of skin or fur to the oil of a plant of the genera Toxicodendron or Rhus which comprises the application of an efficacious amount of aluminum chlorhydrate to fomites.

In a still further embodiment, this invention relates to a method of treating the symptoms of dermatitis or skin irritation in animals caused by exposure to the oil of a plant of the genera Toxicodendron or Rhus which comprises the application of an efficacious amount of aluminum chlorhydrate to the exposed skin or fur.

DETAILED DESCRIPTION OF THE INVENTION

This invention relates to a method of preventing and treating the symptoms of the dermatitis or skin irritation in animals caused by the exposure of skin or fur to the oil of a plant of the genera Toxicodendron or Rhus. Specifically, this invention is directed to the use of an efficacious amount of a compound to prevent and treat the symptoms of the dermatitis or skin irritation caused by the exposure to the oil of a plant of the genera Toxicodendron or Rhus.

Various methods of treating the symptoms of dermatitis or skin irritation caused by the exposure to the oil of a plant of the genera Toxicodendron or Rhus have been suggested in the prior art with little research directed to the prevention of the disease. For example, various chemicals have been suggested as detoxicants, including zirconium, iodine, sodium perborate, and potassium permanganate, for their oxidizing capabilities. However, none have proved more effective than water. Generally, corticosteriods, topical steriods, topical lotions and placebos have been employed to relief itching and other symptoms.

It has been unexpectedly discovered that aluminum chlorhydrate complexes with the alkyl catechols, which cause the allergic reactions in sensitive individuals. Accordingly, the topical application of an effective amount of aluminum chlorhydrate offers a method of preventing the dermatitis or skin irritation caused by exposure to a plant of the genera Toxicodendron or Rhus.

Additionally, the use of an efficacious amount of aluminum chlorhydrate will relieve the symptoms of dermatitis or skin irritation caused by exposure to urushiol oil. This compound is also useful in preventing the spread of the dermatitis or skin irritation once exposure has occured.

The present invention compound is commercially available or can be prepared by art recognized procedures from known compounds or readily preparable intermediates. An exemplary general procedure is as follows: Aluminum metal is treated with a stream of hydrogen chloride gas followed by careful treatment with water.

Fomite is defined for purposes of this application as any object capable of retaining urushiol oil from plants of the genera Toxicodendron or Rhus. Fomites that are contemplated to be within the scope of the present invention include clothes, tools, vehicles, shoes, boots, gloves, articles made of cloth and the like.

It is contemplated that the compound of the present invention can be applied topically to the skin where exposure to the oil of a plant of the genera Toxicodendron or Rhus has occurred or is expected to occur. The compound may be applied before exposure to prevent the development of dermatitis. Alternatively, the compound may be applied following exposure to prevent or control the development of dermatitis, or the compound may be applied after the dermatitis has developed to prevent further spread of the dermatitis. The active ingredient is generally applied to the skin as a composition in combination with any of the below described carriers in a suitable form for topical application.

Additionally, it is contemplated that the compound of the present invention can be applied to fomites, where the oil has collected from a plant of the genera Toxicodendron or Rhus.

The compound may be applied to the fomite before exposure to prevent the development of dermatitis. Alternatively, the compound may be applied following exposure to deactivate the oil present and prevent dermatitis when touched. The active ingredient is generally applied to a fomite in combination with any of the below described suitable carriers. For example, the active ingredient in a compatible aerosol form could be sprayed onto clothing to deactivate the collected urushiol oil and prevent the development of dermatitis that would be expected to occur upon contact with animal skin or fur.

The concentration of aluminum chlorhydrate employed herein at least about 0.5% wt. of the topical composition and can range from about 5% wt. to about 50% wt., preferably from about 20% wt. to about 30% wt. of the topical composition.

Carrier materials suitable for use in the instant compositions include those well-known for use in the cosmetic and medical arts as bases for ointments, lotions, salves, aerosols, and the like. Suitable carriers include, such as for example, water, liquid alcohols, liquid glycols, liquid polyalkylene glycols, liquid esters, liquid amides, liquids protein hydrolysates, liquid alkylated protein hydrolysates, liquid lanolin and lanolin derivatives, and like materials commonly employed in cosmetic and medicinal compositions. Exemplary carriers herein include alcohols, including both monohydric and polyhydric alcohols, e.g., ethanol, isopropanol, glycerol, sorbitol, 2-methoxyethanol diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, and stearoyl diacetin. Oil-in-water emulsions such as cold cream bases can also be used.

Preferably, the carrier herein is a pharmaceutically acceptable liquid alcohol containing from about 2 to about 6 carbon atoms. Mixtures comprising from about 0% to 80% by weight of water and about 20% to 100% by weight of said $C_2$ to $C_6$ alcohols are also suitable. Suitable alcohols herein include ethanol, isopropanol, hexanol, and the like. Especially preferred carriers herein are water-ethanol (ethyl alcohol) mixture at a weight ratio range of about 1:20 to 5:1. Ethanol containing from about 5% by weight of water especially 40:60 volume (i.e., 33.35% by weight) ethanol-water, is preferred as the carrier.

The compositions herein can also include various agents and ingredients commonly employed in dermatological and cosmetic ointments and lotions. For example, perfumes, thickening agents such as carboxymethylcellulose and clays, coloring agents and the like can be present in the compositions to provide a more pleasing aesthetic aspect.

The following examples are presented as specific embodiments of the present invention which show some of its unique characteristics of the present invention, but are not to be considered as constituting a limitation on the present invention.

EXAMPLE 1

Various materials, i.e., those listed in Table I, were tested to determine their ability to complex urushiol on their surfaces or to react to form a chemical complex. The materials used are in various quantities depending on the individual characteristics of the material tested. 3-pentadecylcatechol (PDC) one of the active compounds of urushiol was used to test the effectiveness of each absorbent. The 3-pentadecylcatechol (PDC) solution was stored under nitrogen at $-20°$ C. A respective quantity of absorbent was placed in a vial which was then flushed with dry nitrogen. A 1 ml. sample of PDC in chloroform (2 mg. PDC per ml.) was added and the chloroform evaporated under nitrogen to allow the complete disposition of the PDC on the absorbent. The mixture was then washed with two separate 5 ml. samples of fresh chloroform. The chloroform washings were then combined and evaporated under nitrogen. To this was added 0.250 ml. internal standard (5 mg. dotriacontane per ml. n-heptane), 0.25 ml. dry pyridine, and 0.5 ml n 0-bis (TMS) trifluoroacetamide. After about 30 minutes at 35° C., the sample was analyzed by gas liquid partition chromatography using a Varian Model 1440 flame ionization gas chromatograph with a ⅛ inch 3 percent OV-225/Chromosorb W-HP (80/100) column (column temperature, 215° C.; injector, 225° C.; detector, 225° C.). The retention times of the silated PDC and dotriacontane were approximately 6 minutes and 22 minutes, respectively. The relative areas of these peaks were determined by cutting and weighing.

TABLE 1

|  | Amount of Adsorbent | Physical Form | PDC/int. std.[a] | % PDC Removed |
| --- | --- | --- | --- | --- |
| Blank | — | — | 1.16[b] | — |
| American Colloid Polargel NF (white bentonite) | 2.0 g | powder | 0.20 | 83% |
| American Colloid Magnabrite (magnesium aluminum silicate) | 2.0 g | powder | 0.24 | 79% |
| Calgon carbon | 2.0 g | powder | less than 0.003[c] | 100% |
| Filter Dust (United Desiccants) | 2.0 g | powder | less than 0.009[c] | 100% |
| Regular Product (United Dessiccants) | 2.0 g | ca. ⅛ in. granules | 0.26 | 78% |
| $AlCl_3.6H_2O$ | 2.0 g | crystalline | less than 0.008[c] | 100% |
| Sure, Super Dry | 0.38 g | solid dispersion in liquid (spray) | 0.71 | 39% |
| Sure, Super Dry | 1.84 g | solid dispersion in liquid (spray) | 0.28 | 76% |
| Carbon Filter Dexter #1537 | 0.070 g (4 × 4 cm) (0.025 g Carbon) | paper | 0.38 | 67% |
| Carbon Filter Dexter #3954 | 0.34 g (4 × 4 cm) (0.17 g carbon) | paper | 0.15 | 87% |
| Carbon Filter #4703 | 0.25 g (4 × 4 cm) | paper | 0.018 | 98% |
| Off, Deep-Woods | 1.50 g | liquid spray | 1.14 | 2% |

[a]Area ratios from gas chromatographic (glpc) analyses.
[b]This is the average of two determinations each on two separate experiments. Within a given experiment, glpc ratios agreed within 4%.
[c]No PDC was detected in these experiments. The reported limited was determined by considering the smallest peak which could have been detected by glpc analyses.

All of the materials tested were at least partially successful in deactivating the PDC except for Deep Woods Off. Calgon carbon, filter dust (United Desiccants) and aluminum chlorhydrate ($AlCl_3.6H_2O$ in pure form) were a 100% efficient in PDC deactivation. The other materials (see Table 1) were partly successful depending on their composition.

EXAMPLE 2

A male, age 40, has applied 30% wt. of aluminum chlorhydrate in a topical cream to his hands and arms and was exposed to urushiol oil by direct application to the exposed area of his skin. The aluminum chlorhydrate prevents the dermatitis or skin irritation caused such exposure.

EXAMPLE 3

A male, age 40, has sprayed 25% wt. of aluminum chlorhydrate in an aerosol form to his hands and arms and was exposed to urushiol oil by direct application to the treated skin area. The aluminum chlorhydrate prevents the dermatitis or skin irritation caused by such exposure.

EXAMPLE 4

A female, age 39, has poison ivy dermatitis on her hands and arms. An application of 30% wt. of aluminum chlorhydrate in a lotion to the affected area relieves the symptoms of the dermatitis and prevents further spread of the dermatitis.

EXAMPLE 5

A female, age 45, has poison oak dermatitis on her legs and feet. An application of 25% wt. of aluminum chlorhydrate in aerosol form to the affected area relieves the symptoms and prevents further spread of the dermatitis.

Obviously, other modifications and variations of the present invention are possible in the light of the above teachings. It is, therefore, to be understood that changes which are within the full intended scope of the invention as defined by the appended claims.

What is claimed is:

1. A method for the prevention of dermatitis or skin irritation in animals caused by exposure to the oil of a plant of the genera Toxicodendron or Rhus, which comprises the topical application to the exposed skin or fur of a topical composition comprising an effective amount of aluminum chlorhydrate.

2. The method according to claim 1, wherein said aluminum chlorhydrate is present in about 5% wt. to about 50% wt. of said composition.

3. The method according to claim 1, wherein said composition is applied as a pharmaceutically acceptable topical preparation.

4. The method according to claim 1, wherein said composition is applied as a water solution.

5. The method according to claim 1, wherein said composition is applied as an alcohol solution.

6. The method according to claim 1, wherein said composition is applied as an aqueous-alcohol solution.

7. The method according to claim 1, wherein said composition is applied in a halogenated hydrocarbon propellent solution.

8. The method according to claim 7, wherein said propellent solution is a 1:1 mixture of trichlorofluoromethane and dichlordifluoromethane.

9. A method of preventing the dermatitis or skin irritation in animals caused by the exposure to the oil of a plant of the genera Toxicodendron or Rhus, which comprises the application to a fomite of a composition comprising an effective amount of aluminum chlorhydrate.

10. The method according to claim 9, wherein said aluminum chlrohydrate is present in about 5% wt. to about 50% wt. of said composition.

11. The method according to claim 9, wherein said composition is applied as a pharmaceutically acceptable topical preparation.

12. The method according to claim 9, wherein said composition is applied as a water solution.

13. The method according to claim 9, wherein said compound is applied as an alcohol solution.

14. The method according to claim 9, wherein said composition is applied as an aqueous-alcohol solution.

15. The method according to claim 9, wherein said composition is applied in a halogenated hydrocarbon propellent solution.

16. The method according to claim 15, wherein said propellent solution is a 1:1 mixture of trichlorofluoromethane and dichlorodiflouromethane.

* * * * *